United States Patent [19]

Belcour et al.

[11] Patent Number: 5,691,172

[45] Date of Patent: Nov. 25, 1997

[54] COSMETIC COMPOSITION CONTAINING AS COLORANT AT LEAST ONE 5-METHOXY-8-METHYL-2-PHENYL-7H-1-BENZOPYRAN-7-ONE DERIVATIVE

[75] Inventors: Béatrice Belcour, Tours; Richard Martin, Vouvray; Georges Hussler, Aulnay-Sous-Bois, all of France

[73] Assignee: L'Oreal, Paris, France

[21] Appl. No.: 379,654

[22] PCT Filed: Jun. 10, 1994

[86] PCT No.: PCT/FR94/00695

§ 371 Date: Aug. 31, 1995

§ 102(e) Date: Aug. 31, 1995

[87] PCT Pub. No.: WO94/29388

PCT Pub. Date: Dec. 22, 1994

[30] Foreign Application Priority Data

Jun. 10, 1993 [FR] France ................... 93 07002

[51] Int. Cl.$^6$ ............ A61K 7/00; C09B 61/00; C12P 17/06; C07D 311/60
[52] U.S. Cl. ........... 435/125; 549/406; 514/456; 424/401
[58] Field of Search ............ 549/406; 514/456; 435/125; 424/401

[56] References Cited

FOREIGN PATENT DOCUMENTS 0387739  9/1990  European Pat. Off. .

OTHER PUBLICATIONS

Japanese Patents Gazette, Week 8636, Derwent Publications, AN 86-236264 & JP A-61 166 396, 1986.
Database WPI, Week 8907, Derwent Publications, AN 89-051783 & JP-A-64 002 593, 1989.
Brockman et al, "Ueber Benzopyrylium Verbindungen", Chemische Berichte, vol. 77, No. 5, May 1944, pp. 347–353.

Figueras et al, "Rote Farbpigmente fur dekorative Kosemtika", Seifen/Oele/Fette/Wachse, vol. 113, No. 10, Jun. 1987, pp. 335–336.

Database WPI, Week 9042, Derwent Publications, AN 90-315507 & JP-A-2 222 691, 1990.

*Primary Examiner*—José G. Dees
*Assistant Examiner*—Laura L. Stockton
*Attorney, Agent, or Firm*—Nixon & Vanderhye, P.C.

[57] ABSTRACT

A cosmetic composition containing at least one derivative of 5-methoxy 8-methyl 2-phenyl 7H-1-benzopyran-7-one, the method of preparing these derivatives, and novel derivatives are disclosed. The cosmetic composition contains at least one compound of formula (I)

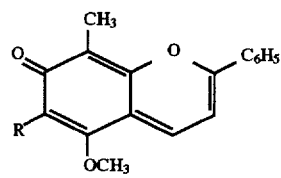

as a coloring in a suitable cosmetic carrier, wherein R is a methyl, hydroxymethyl, or methoxymethyl radical. The cosmetic compositions may include lipsticks, nail varnishes, hair lotions and face make-up products.

21 Claims, No Drawings

COSMETIC COMPOSITION CONTAINING AS COLORANT AT LEAST ONE 5-METHOXY-8-METHYL-2-PHENYL-7H-1-BENZOPYRAN-7-ONE DERIVATIVE

This application is a 371 of PCT/FR94/00695 filed Jun. 10, 1994.

The invention relates to a cosmetic composition which contains as colorant at least one 5-methoxy-8-methyl-2-phenyl-7H-1-benzopyran-7-one derivative.

The present invention relates more particularly to a cosmetic composition containing as colorant a mixture of 5-methoxy-8-methyl-2-phenyl-7H-1-benzopyran-7-one derivatives obtained from tissue cultures of Basella rubra, in an appropriate medium.

It is well known that the majority of cosmetic compositions, whether intended for make-up or for skin care or hair care, contain variable concentrations of at least one colorant which may be of the pigment type and is intended either for colouring the nails, lips or hair or for giving the composition a certain colouration which enhances its visual appearance.

Numerous colorants have already been proposed for incorporation into cosmetic compositions such as, for example, lipsticks, nail varnishes, hair lotions and into make-up products for the face, in the form of foundations or creams of varying fluidity.

Up until now the choice of colorants has been dependent on the nature of the cosmetic compositions, which constitutes a serious disadvantage inasmuch as numerous tests must be carried out to determine the selection of these colorants.

It has now surprisingly been found that it is possible to use a certain class of colorants universally in cosmetic compositions, which colorants are essentially red to dark red and are derivatives of 5-methoxy-8-methyl-2-phenyl-7H-1-benzopyran-7-one.

One subject of the present invention is therefore a cosmetic composition containing as colorant, in a suitable cosmetic excipient, at least one compound corresponding to the following formula (I):

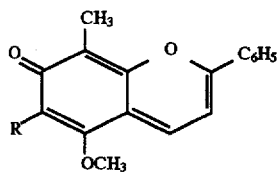
(I)

in which:
R represents a methyl, hydroxymethyl or methoxymethyl radical.

The compounds of formula (I) are more particularly the following:

5-methoxy-6,8-dimethyl-2-phenyl-7H-1-benzopyran-7-one (compound Ia), 5-methoxy-6-hydroxymethyl-8-methyl-2-phenyl-7H-1-benzo-pyran-7-one (compound Ib), and 5-methoxy-6-methoxymethyl-8-methyl-2-phenyl-7H-1-benzo-pyran-7-one (compound Ic).

Compound Ia is a known compound whose preparation has been described by Borckmann et al., Chemische Berichte, vol. 77, No. 5, pp. 347–353, 1944.

Compounds Ib and Ic are novel and can be obtained according to the same procedure. These compounds also constitute one of the subjects of the invention.

The compounds of the formula (I) and, in particular, mixtures thereof may also be obtained by culturing calluses of Basella rubra.

Another subject of the present invention is therefore a novel process for preparing red colorants from calluses obtained by tissue culture of Basella rubra in an appropriate medium.

The patent application JP 166 396 describes the preparation of red colorants from calluses obtained by tissue culture of Basella rubra in a medium supplemented with an auxin such as 2,4-dichlorophenoxyacetic acid (2,4-D) and with a cytokinin such as kinetin, followed by a step of production of colorants by culturing the said calluses in the dark on a culture medium containing, for the purpose of increasing the yield, a combination of an auxin such as naphthaleneacetic acid (NAA) and a cytokinin such as kinetin or benzyladenine.

The colorant substances obtained in accordance with the process described in this application are colorants which are already present in the plant of origin.

Surprisingly and unexpectedly it has been found that, when calluses of Basella rubra are produced in a first culture medium in the presence of naphthaleneacetic acid and a cytokinin and the calluses obtained are transferred and cultured in a nutrient medium containing 2,4-dichlorophenoxyacetic acid (2,4-D), it is possible to obtain, in this second medium and without carrying out any special operations, colorants which differ from those described in the application JP 166 396 and which are not present in the plant of origin.

This particularly surprising result is caused essentially by the fact that, in contrast to the patent application JP 166 396, the process of the invention uses in the second culture medium, instead of naphthalene-acetic acid, 2,4-dichlorophenoxyacetic acid, and because of the fact, moreover, that it uses in the first culture medium naphthaleneacetic acid in combination with a cytokinin.

Another subject of the present invention, therefore, is a process for the preparation of at least one colorant corresponding to the general formula (I), which process consists in preparing and culturing calluses of Basella rubra in a first, suitable nutrient medium containing naphthaleneacetic acid and a cytokinin, then in transferring the calluses obtained to a second nutrient medium referred to as the transfer medium, and culturing them therein, this medium containing an auxin which is 2,4-dichlorophenoxyacetic acid, in separating the transfer medium from the biomass and in subjecting the said transfer medium to an extraction and, optionally, in isolating at least one of the compounds of formula (I) by known methods.

In a particular embodiment of the process according to the invention, the process may also have the following characteristics, taken individually or, if desired, in combination:

the cytokinin in the first culture medium is preferably kinetin;

the second nutrient medium additionally contains a cytokinin, especially kinetin;

the step of preparation of the calluses is carried out under lighting which is sufficient to obtain chloro-phyllian calluses, whereas the step of biosynthesis of the colorants after transfer of the calluses to the second nutrient medium may be carried out either in darkness or in light;

the first and the second nutrient medium are of the Murashige and Skoog type; and the calluses used are calluses of Basella rubra, variety alba.

As mentioned above, after a sufficient culture time, the transfer medium is separated from the biomass and is subjected to an extraction using a solvent which may be chosen from dichloromethane, methanol, ethyl acetate and chloroform or mixtures thereof. When a water-miscible solvent such as methanol is used, the water is first of all removed before the residue is taken up in this solvent.

The extract obtained after concentration may, if desired, be purified with the purpose of isolating by known methods, for example by thin-layer or column chromatography, the compounds Ia, Ib and Ic as defined above.

Yet another subject of the present invention is a compound corresponding to the following general formula (II):

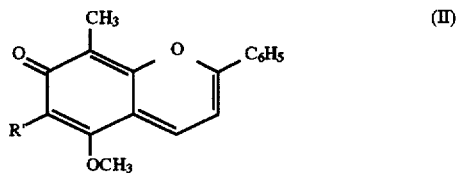

in which:

R' represents a hydroxymethyl or methoxymethyl radical.

The compounds of formula (II) are more particularly the following:

5-methoxy-6-hydroxymethyl-8-methyl-2-phenyl-7H-1-benzopyran-7-one, and 5-methoxy-6-methoxymethyl-8-methyl-2-phenyl-7H-1-benzopyran-7-one.

It is self-evident that, in accordance with the principal subject of the invention, namely the cosmetic compositions, the colorant may be in the form of an extract, that is to say in the form of a mixture or in the form of an individual compound which is isolated by the process described above or obtained by way of organic synthesis.

In the cosmetic compositions according to the invention, the concentration of colorant as defined above is generally between 0.001 and 20% by weight relative to total weight of the composition.

When the colorant is intended more particularly for make-up products such as lipsticks, nail varnishes, powders or else foundations, the concentration is preferably between 0.1 and 20% by weight and more particularly between 0.5 and 10% by weight relative to the total weight of the composition.

In contrast, when the colorant is intended solely to impart colouration to cosmetic compositions such as, for example, creams, oily gels or face masks, the concentration is in this case markedly lower and is preferably between 0.0001 and 1% by weight relative to the total weight of the composition.

When the compositions according to the invention are intended for use on hair, with the purpose of imparting to the latter a certain colouration, the concentration of colorant is generally between 0.05 and 10% by weight and preferably between 0.1 and 2.5% by weight relative to the total weight of the composition.

A conclusion from the abovementioned percentages is that the concentration of colorant may vary within wide limits and depends essentially on the intensity of colouration which it is desired to impart.

According to the invention, the cosmetic compositions may be liquid, semi-solid or solid and may be presented in various forms such as, for example, in the form of sticks, pastes, anhydrous or aqueous creams, emulsions, suspensions, dispersions or solutions and may consist of lipsticks, mascaras, rouges, eyeshadows, foundations, compact or other powders, or else nail varnishes.

According to the invention, the colorant as defined above may be combined with mineral or organic pigments, especially lakes, such as D & C Red No. 7 calcium lakes, D & C Red No. 6 and 9 barium lakes, D & C Red No. 3 and D & C Yellow No. 5 aluminium lakes and D & C Orange No. 5 zirconium lakes. D & C Red 30 and 36 may also be included in this list: because of their insolubility in water and in oils they are generally considered as being pigments although they are not present in the form of metal lakes.

Among the inorganic pigments, particular mention may be made of iron oxides (red, brown, black and yellow), chromium oxides, ultramarines (polysulphides of aminosilicates), titanium dioxide, manganese pyrophosphate and Prussian blue (ferric ferrocyanide). These various compounds, individually or in the form of a mixture, are generally employed at a concentration of between 0.1 and 40% relative to the total weight of the composition.

Moreover, these compositions may also contain nacreous agents such as bismuth oxychloride, titanium dioxide-coating mica and crystals of guanine.

When the compositions are presented in the form of sticks, especially for lipsticks, eyeshadows, rouges and foundations, an important part of these compositions consists of the fatty substance which may be at least one wax such as, for example, ozokerite, lanolin, lanolin alcohol, hydrogenated lanolin, acetylated lanolin, lanolin wax, beeswax, candellila wax, microcrystalline wax, carnauba wax, cetyl alcohol, stearyl alcohol, cocoa butter, tanoline fatty acids, petrolatum, petroleum jellies, mono-, di- and triglycerides which are solid at 25° C., fatty esters which are solid at 25° C., silicone waxes such as methyl octadecan-oxypolysiloxane and poly(dimethylsiloxy)stearoxysiloxane, stearic monoethanolamide, colophony and derivatives thereof such as glycol and glycerol abietates, hydrogenated oils which are solid at 25° C., and sucroglycerides and oleates, myristates, lanolates, stearates and dihydroxystearates of calcium, magnesium, zirconium and aluminium.

The fatty substance may also consist of a mixture of at least one wax and at least one oil, in which case the oil may be, for example: paraffin oil, purcellin oil, perhydrosqualene oil, sweet almond oil, avocado oil, calophyllura oil, caster oil, sesame oil, jojoba oil, mineral oils having a boiling point between 310° and 410° C., silicone oils such as dimethylpolysiloxanes, linoleyl alcohol, linolenyl alcohol, oleyl alcohol, wheatgerm oil, isopropyl lanolate,.isopropyl palmitate, isopropyl myristate, methyl myristate, cetyl myristate, hexadecyl stearate, butyl stearate, decyl oleate, acetyl-glycerides, octanoates and decanoates of alcohols and of polyalcohols such as those of glycol and of glycerol, ricinoleates of alcohols and of polyalcohols such as cetyl ricinoleate, isostearyl alcohol, isocetyl lanolate, isopropyl adipate, hexyl laurate and octyldodecanol.

The fatty substance in these compositions in stick form may generally represent up to 99%, alternatively 99.9%, by weight of the total weight of the composition.

These cosmetic compositions may also contain other ingredients, such as for example, glycols, polyethylene glycols, polypropylene glycols, monoalkanolamides, colourless polymers, inorganic or organic fillers, preservatives, UV filters or other additives which are commonplace in cosmetics.

These compositions in stick form are preferably anhydrous. However, in certain cases they may contain a certain quantity of water which generally does not exceed 40% relative to the total weight of the stick.

When the cosmetic compositions according to the invention are presented in semi-solid form, that is to say in the form of pastes or creams, they may be either anhydrous or aqueous and constitute foundations, rouges, eyeshadows, lipsticks, etc.

When these pastes or creams are, on the other hand, aqueous, they are then more particularly emulsions of the water-in-oil or oil-in-water type in which the fatty phase represents from 1 to 98.8% by weight, the water phase from 1 to 98.8% and the emulsifier from 0.1 to 30% by weight.

These compositions may also contain other conventional ingredients such as fragrances, antioxidants, preservatives, gelling agents, UV filters, dyes, pigments, nacreous agents, colourless polymers and inorganic or organic fillers.

When the cosmetic compositions according to the invention are presented in the form of a powder, they consist essentially of an inorganic or organic filler such as talc, kaolin, starches, polyethylene powders or polyamide powders and of additives such as kaolin, starches, polyethylene powders or polyamide powders and of additives such as binders, dyes, etc.

Compositions of this kind may also contain various additives which are conventional in cosmetics, such as fragrances, antioxidants, preservatives, etc.

When the compositions according to the invention are presented in the form of nail varnishes they consist essentially of nitrocellulose and a natural or synthetic polymer, in solution in a solvent system, or a varnish base which solution optionally contains other additives such as pigments and/or nacreous agents.

When the compositions according to the invention are intended for hair-care use they may be presented in the form of lotions, emulsions, thickened lotions or gels.

When the hair-care compositions are presented in the form of lotions, they generally comprise the colorant in aqueous, alcoholic or aqueous-alcoholic solution, as well as various additives which are conventional in this type of composition.

These compositions may also be presented in the form of an aerosol comprising a propellent gas such as gaseous carbon dioxide, nitrogen, nitrous oxide, volatile hydrocarbons such as butane, isobutane or propane, or else halogenated hydrocarbons.

When the compositions are presented in the form of emulsions, these may be nonionic or anionic. Nonionic emulsions consist principally of a mixture of oil and/or fatty alcohol and of a polyethoxylated alcohol such as polyethoxylated stearyl or cetearyl alcohols. Cationic surfactants may be added, if desired, to these compositions.

The anionic emulsions are constituted essentially from soaps.

When the compositions are presented in the form of thickened lotions or gels, they contain thickeners in the presence or absence of solvents. The thickeners which can be used may be sodium alginate, gum arabic or xanthan gum, or cellulosic derivatives such as methylcellulose, hydroxymethylcellulose, hydroxyethylcellulose, hydroxypropylcellulose, hydroxypropylmethylcellulose or carboxymethylcellulose. The lotions may also be thickened by mixing polyethylene glycol and polyethylene glycol stearate or distearate or by means of a mixture of phosphate and amide. The concentration of thickener may vary from 0.5 to 30% by weight, advantageously from 0.5 to 15% by weight and preferably from 0.5 to 5%. The pH of the lotions varies essentially between 3 and 9 and preferably between 4.5 and 7.5.

By way of illustration, an example will now be given for the preparation of the colorants of formula (I) and of several examples of cosmetic compositions according to the invention.

EXAMPLE 1 a) The plant used is *Basella rubra*, variety *alba*, with leaves and green stems.

Explants are taken of stems and/or of leaf petioles, having a length of approximately 0.5 cm.

The explants are disinfected by immersion in a solution of mercuric chloride at a concentration of 1 for one minute and 30 seconds and are then rinsed three times in succession with sterile water in order to remove the residues of mercuric chloride.

The explants are placed under aseptic conditions in culture dishes containing an agar culture medium A consisting essentially of a nutrient medium of Murashige and Skoog type supplemented with naphthaleneacetic acid (1 mg/l) and with kinetin (1 mg/l).

The culture conditions are as follows:

lighting conditions: 5 µ-Einstein/m$^2$/s;

photoperiod: 16 h;

culture temperature: 26° C.

The culture dishes are Petri dishes with a diameter of 45 mm which each contain 12 ml of culture medium.

After one month primary calluses are obtained which are of chlorophyllian type and show root emergence.

These callus cultures may be maintained by monthly transplantation.

b) Transfer to liquid medium

Plant tissues obtained after seven transplantation cycles and after culture in accordance with method a) above are transferred to a liquid medium. For this purpose, 2 g of tissues obtained after 1 month of culture as described in a) are transferred to a 100 ml conical flask containing 50 ml of medium A' (medium A minus agar). The flasks are stirred at 100 rpm, at 26° C. under lighting of 5 µ-Einstein/m$^2$/s (photoperiod of 12 hours). After 8 days of culture under these conditions, the appearance and development of structures of globular type are observed.

These tissues may be maintained by periodic transplantation, every 15 days for example, after filtration and inoculation in a new medium A'.

c) Induction of the formation of coloured metabolites

15-Day tissue cultures on medium A' are filtered over 50 µm Blutex cloth and then are divided under sterile conditions into 250 ml conical flasks containing 100 ml of nutrient medium B, inoculation being carried out at a concentration of 25 g/l.

Medium B consists of a nutrient medium of Mdrashige and Skoog type supplemented with 2,4-D (1 mg/l) and with kinetin (1 mg/l).

The culture conditions are as follows:

stirring at 100 rpm;

lighting: 5 micro-Einsteins per m$^2$/s;

photoperiod: 12 hours;

temperature: 26° C.

At the end of a latency period of 24–48 hours, the appearance of a pink colouration is observed in the culture medium.

Study of the coloured metabolites in the tissues and in the culture medium at different stages in the biosynthesis shows that these metabolites are not stored by the cells but diffuse into the medium.

The biosynthesis of the metabolites is accompanied by an absence of tissue growth.

To ensure continuity of production, the culture medium may be renewed. For this, the culture medium containing the coloured metabolites is separated by filtration on a 50 µm Blutex cloth. The collected tissues are taken up and transferred, under the same conditions of inoculation and culture, in a new, sterile medium B.

In addition, similar cultures were carried out in media which were analogous to the medium B but supplemented with different concentrations of 2,4-D (2.5, 5, 7.5 and 10 mg/l).

It was noted that the production of coloured metabolites increases with the content of 2,4-D in the medium.

Effect of Renewing the Medium

The production medium can be renewed. For this, the culture is filtered, for example, on a 50 μm Blutex cloth and the plant tissues are transferred, under the same conditions of inoculation and culture, into a new, supplemented medium B. It was observed that, under these conditions, the productivity after renewal of the medium is increased by a factor of 1.4.

Effect of Lighting

The coloured metabolites may be produced with lighting or in the dark. In the dark, the yield may be doubled but the respective proportions of compounds Ib and Ia are different depending on the lighting conditions.

Extraction of the Compounds

The culture media separated by filtration as described above are acidified with 1 N hydrochloric acid to a pH of 2.5. They are then extracted twice in succession by one volume of dichloromethane with stirring for one hour in each case.

In the case of agar culture media, three extractions are carried out in succession with one volume of methanol.

The organic extracts obtained are subsequently concentrated to dryness under reduced pressure at 50° C. and the residue is redissolved in methanol and then analysed by thin-layer chromatography on a silica plate (from Merck, Kieselgel 60 F2-54) using as eluent a 95:5 (v/v) mixture of dichloromethane/methanol. 3 compounds are distinguished, which are characterized respectively by the $R_f$ of 0.45, 0.40 and 0.30.

Subsequent analysis of the compounds showed that the compound with an $R_f$ of 0.45 is compound Ia, that with an $R_f$ of 0.30 is compound Ib and that with an $R_f$ of 0.40 is compound Ic.

Compounds Ia and Ib were isolated by medium-pressure chromatography on a silica column using a 94:6 mixture of dichloromethane/methanol as eluent. This separation made it possible to collect, in addition, a fraction enriched in compound Ic, which was subsequently purified by thin-layer chromatography (silica; eluent: 0:20:10 ethyl acetate/dichloromethane/heptane).

Medium-pressure chromatography was carried out using the silica marketed under the name Merck Kieselgel (40–63 μm).

Medium-pressure chromatography of 400 mg of extracts, collecting 25 ml fractions, was carried out using a 96:4 eluent mixture of dichloromethane/methanol. For an extract obtained on a 14- to 16-day culture on medium B, 52 mg of compound Ia, 41 mg of compound Ib and 18 mg of a mixture enriched in compound Ic were obtained. 1.3 mg of compound Ic were obtained by thin-layer chromatography using as eluent a 70:20:10 mixture of ethyl acetate/dichloromethane/heptane and then a 93:7 mixture of dichloromethane/methanol.

On the basis of this column fractionation, the extract obtained above contains approximately:

13% of compound Ia
10.2% of compound Ib
0.3% of compound Ic.

The structure of compounds Ia, Ib and Ic was established by means of analysis by mass spectrometry, UV spectroscopy, IR spectroscopy, $^1$H NMR spectroscopy, $^{13}$C NMR spectroscopy, and by a combination of $^2$D NMR with $^1$H-$^{13}$C heteronuclear correlation and inverse-detection long-range coupling.

The infrared spectra were recorded by deposition and evaporation of a solution of compounds Ia, Ib and Ic in chloroform on a NaCl window using a Brucker IFS 85 instrument.

The UV spectra were recorded in chloroform on a Shimadzu UV 2101 PC instrument.

The mass spectra were obtained with EI using an Incos 50 quadrapolar-type spectrometer (Finnigan).

The $^1$H-$^{13}$C and 2D NMR spectra were run on a Brucker AMX 500 MHz instrument, using deuterated chloroform as internal standard.

These analyses made it possible to establish the structure which is that indicated above.

By way of example, the absorption spectrum (UV) in ethanol shows the following maxima:

compound Ia: 495, 375, 326 and 255 nm.

compound Ib: 503, 365, 325, 275 and 244 nm.

Direct dyeing tests at spontaneous pH on locks of hair proved positive. The colouring power of the compounds of the invention was also observed on various substrates such as nylon cloths, silicone polymers, etc.

Stability of Colouration a) Stability to light and heat

Tests were carried out on crude extracts by exposure to light at 254 nm for 6 hours or to heat by maintaining the crude extracts for 6 hours at a temperature of 50° or 80° C. No modification in colour is observed.

Moreover, the colourations obtained on substrates show a good resistance to washing.

With analogous treatment but at 100° C., the initial pinkish-red colour of the control extract takes on a modified orange-red shade.

b) Stability to pH

The crude extract in aqueous phase at a pH of between 3.5 and 10.5 shows no variation in colour (pinkish-red).

At a pH lower than 3.5 and at a pH greater than 10.5, the initial pinkish-red colour takes on a modified orange-red shade.

EXAMPLE 2

Hair-dyeing composition in the form of a lotion containing the following ingredients:

Extract of callus culture of *Basella rubra*,

| | | |
|---|---|---|
| obtained in accordance with Example 1 | | 0.80 g |
| 96% ethanol (vol/vol) | | 30.00 g |
| Triethanolamine | qs | pH = 8 |
| Water | qs | 100.00 g |

A lock of 0.15 g of permanent-waved grey hair (containing 90% of white hairs) is immersed in 10 g of the above dyeing composition for 30 minutes.

After rinsing and drying, the hair is coloured in a pink shade.

EXAMPLE 3

Hair-dyeing composition in the form of a lotion containing the following ingredients:

| | |
|---|---|
| Extract of callus culture of *Basella rubra*, obtained in accordance with Example 1 | 0.23 g |

9
-continued

| | | |
|---|---|---|
| Vinyl pyrrolidone/vinyl acetate copolymer (65/35) | | 1.50 g |
| 96% ethanol (vol/vol) | | 30.00 g |
| 2-amino-2-methyl-1-propanol | qs | pH = 9 |
| Water | qs | 100.00 g |

0.15 g of this dyeing composition is applied per g of natural grey hair (containing 90% of white hairs). After a waiting time of 30 minutes followed by drying, the hair is coloured in a very light ash blond shade.

EXAMPLE 4

Cosmetic composition in the form of lipstick containing the following ingredients:

| | | |
|---|---|---|
| Liquid lanolin | | 19.50 g |
| Microcrystalline wax | | 15.00 g |
| Capric/caprylic triglycerides sold under the name "Miglyol 812" by the company Hüls AG | | 11.00 g |
| Octylglyceryl behenate | | 11.00 g |
| Sesame oil | | 10.00 g |
| Titanium oxide | | 3.00 g |
| Extract of callus culture of *Basella rubra* obtained in accordance with Example 1 | | 3.00 g |
| Butylated hydroxytoluene | | 0.20 g |
| Castor oil | qs | 100.00 g |

EXAMPLE 5

Cosmetic composition in the form of a rouge containing:

| | | |
|---|---|---|
| Liquid petroleum | | 6.00 g |
| Titanium dioxide-coated mica | | 10.00 g |
| Titanium dioxide | | 10.00 g |
| Red iron oxide | | 0.90 g |
| Black iron oxide | | 0.10 g |
| Extract of callus culture of *Basella rubra*, obtained in accordance with Example 1 | | 1.20 g |
| Talc | qs | 100.00 g |

EXAMPLE 6

Cosmetic composition in the form of a pressed face powder, containing:

| | | |
|---|---|---|
| Mica | | 10.00 g |
| Nylon powder | | 10.00 g |
| Titanium dioxide | | 10.00 g |
| Isopropyl myristate | | 1.50 g |
| Liquid petroleum | | 1.50 g |
| Extract of callus culture of *Basella rubra*, obtained in accordance with Example 1 | | 0.50 g |
| Iron oxides | | 3.00 g |
| Talc | qs | 100.00 g |

EXAMPLE 7

Cosmetic composition in the form of a day cream containing:

| | |
|---|---|
| Auto-emulsifiable glycerol stearate sold under the name "ARLACEL 165" by the Company ICI | 3.00 g |
| Cetearyl alcohol | 1.50 g |
| Triethanolamine | 0.40 g |
| Homopolymer of crosslinked acrylic acid | 0.40 g |

10
-continued

| | | |
|---|---|---|
| (Carbomer) | | |
| Apricot oil | | 12.00 g |
| Polyisobutene | | 6.00 g |
| Sodium pyrrolidonecarboxylate | | 3.00 g |
| Cyclopentadimethylsiloxane | | 5.00 g |
| Imidazolidinylurea sold under the name "Germall 115" by the Company Sutton | | 0.20 g |
| Extract of callus culture of *Basella rubra*, obtained in accordance with Example 1 | | 0.005 g |
| Yellow iron oxide | | 0.001 g |
| Preservatives | | 0.30 g |
| Water | qs | 100.00 g |

We claim:

1. A cosmetic composition, comprising a colorant, in a suitable cosmetic excipient, said colorant being at least one compound corresponding to the following formula:

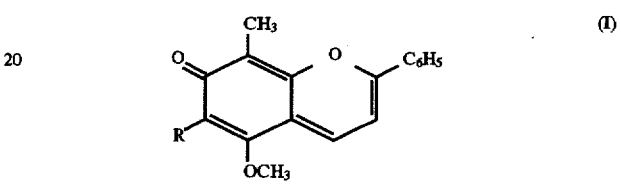

in which:
R represents a methyl, hydroxymethyl or methoxymethyl radical.

2. The composition according to claim 1, wherein said colorant is selected from the group consisting of 5-methoxy-6,8-dimethyl-2-phenyl-7H-1-benzopyran-7-one; 5-methoxy-6-hydroxymethyl-8-methyl-2-phenyl-7H-1-benzopyran-7-one; 5-methoxy-6-methoxymethyl-8-methyl-2-phenyl-7H-1-benzopyran-7-one; and mixtures thereof.

3. The composition according to claim 1 in the form of a liquid, a semi-solid or a solid.

4. The composition according to claim 1 wherein said colorant is present in a proportion of between 0.0001 and 20% by weight relative to the total weight of the composition.

5. The composition according to claim 1 in the form of a stick containing from 0.1 to 20% by weight of said colorant and up to 99.9% by weight of a fatty substance consisting of at least one wax and, optionally, at least one oil.

6. The composition according to claim 5, containing up to 40% by weight of water relative to the total weight of the composition.

7. The composition according to claim 1 in the form of a paste or an anhydrous cream or an aqueous cream.

8. The composition according to claim 1 in the form of a water-in-oil or oil-in-water emulsion containing a fatty phase, a water phase and an emulsifier, the fatty phase representing from 1 to 98.8% by weight, the water phase from 1 to 98.8% by weight, and the emulsifier from 0.1 to 30% by weight relative to the total weight of the composition.

9. The composition according to claim 1 in the form of a pressed powder containing a filler selected from the group consisting of talc, kaolin, starch, polyethylene powder and polyamide powder.

10. The composition according to claim 1 in the form of a nail varnish containing, in a varnish base, from 0.1 to 20% by weight of said colorant.

11. The composition according to claim 1 in the form of an aqueous, alcoholic or aqueous-alcoholic hair lotion containing the said colorant in a proportion of between 0.05 and 10% by weight relative to the total weight of the composition.

12. The composition according to claim 11 wherein said colorant is present in an amount of between 0.1 and 2.5% by weight relative to the total weight of the composition.

13. A process for preparing a colorant of the following formula:

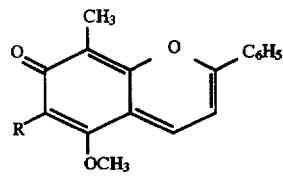

wherein R represents a methyl, hydroxy methyl or methoxymethyl radical, said method comprising the steps of:
- preparing and culturing calluses of *Basella rubra* in a first, suitable nutrient medium containing, as auxin, naphthalene acetic acid and a cytokinin,
- transferring the calluses obtained to a second nutrient medium, referred to as the transfer medium, and
- culturing said calluses in said transfer medium containing, as auxin, 2,4-dichlorophenoxyacetic acid, to obtain a biomass
- separating the transfer medium from said biomass,
- subjecting the said transfer medium to an extraction and, optionally,
- isolating the compounds of formula (I) from the extract.

14. The process according to claim 13, wherein said transfer medium additionally contains a cytokinin.

15. The process according to claim 14 wherein said cytokinin is kinetin.

16. The process according to claim 13 wherein said preparing calluses further comprises using lighting which is sufficient to obtain chlorophyllian calluses.

17. The process according to claim 13, wherein the said first and said second nutrient medium are Murashige and Skoog medium.

18. The process according to claim 13 wherein said calluses are obtained from *Basella rubra*, variety *alba*.

19. The process according to claim 13, comprising performing said extraction with at least one solvent selected from the group consisting of dichloromethane, methanol, ethyl acetate and chloroform.

20. A compound of the formula (II):

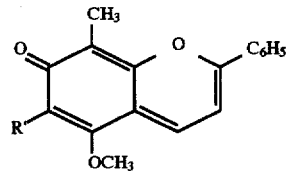

in which:

R' represents a hydroxymethyl or methoxymethyl radical.

21. The compound according to claim 20, selected from the group consisting of 5-methoxy-6-hydroxymethyl-8-methyl-2-phenyl-7H-1-benzopyran-7-one; and 5-methoxy-6-methoxymethyl-8-methyl-2-phenyl-7H-1-benzo-pyran-7-one.

* * * * *